US012807584B2

(12) United States Patent
Zeng et al.

(10) Patent No.: US 12,807,584 B2
(45) Date of Patent: Nov. 24, 2026

(54) METHOD FOR PREPARING 2,5-BISHYDROXYMETHYLFURAN USING 5-CHLOROMETHYLFURFURAL

(71) Applicant: Xiamen University, Xiamen (CN)

(72) Inventors: Xianhai Zeng, Xiamen (CN); Binglin Chen, Xiamen (CN); Gaofeng Chen, Xiamen (CN); Ye Tian, Xiamen (CN); Zheng Li, Xiamen (CN); Shuliang Yang, Xiamen (CN); Xing Tang, Xiamen (CN); Yong Sun, Xiamen (CN); Lu Lin, Xiamen (CN)

(73) Assignee: Xiamen University, Xiamen (CN)

( * ) Notice: Subject to any disclaimer, the term of this patent is extended or adjusted under 35 U.S.C. 154(b) by 366 days.

(21) Appl. No.: 18/655,540

(22) Filed: May 6, 2024

(65) Prior Publication Data

US 2024/0294485 A1 Sep. 5, 2024

Related U.S. Application Data

(63) Continuation of application No. PCT/CN2022/099830, filed on Jun. 20, 2022.

(30) Foreign Application Priority Data

Nov. 4, 2021 (CN) ......................... 202111298723.0

(51) Int. Cl.
*C07D 307/42* (2006.01)
*B01J 23/89* (2006.01)

(52) U.S. Cl.
CPC ........ *C07D 307/42* (2013.01); *B01J 23/8913* (2013.01); *B01J 23/8926* (2013.01)

(58) Field of Classification Search
None
See application file for complete search history.

(56) References Cited

FOREIGN PATENT DOCUMENTS

| | | | |
|---|---|---|---|
| CN | 103804329 | A | 5/2014 |
| CN | 104607202 | A | 5/2015 |
| CN | 110128378 | A | 8/2019 |
| CN | 112341414 | A | 2/2021 |
| CN | 112574142 | A | 3/2021 |
| CN | 114105914 | A | 3/2022 |

OTHER PUBLICATIONS

Kang et al., ChemSusChem (2015), 8(11), 1179-1188 (Year: 2015).*
Vikanova, Kseniia, et al., "Advanced Room-Temperature Synthesis of 2,5-Bis(hydroxymethyl)furan-A Monomer for Biopolymers-From 5-Hydroxymethylfurfural", ACS Sustainable Chemical Engineering, Mar. 9, 2021, pp. 1161-1171, vol. 9, Issue 3.

(Continued)

*Primary Examiner* — George W Kosturko
*Assistant Examiner* — Jason M. Nolan
(74) *Attorney, Agent, or Firm* — Cooper Legal Group, LLC

(57) ABSTRACT

A method for preparing 2,5-bishydroxymethylfuran using 5-chloromethylfurfural, the 5-chloromethylfurfural is transformed into the 2,5-bishydroxymethylfuran using a catalyst, a base neutralizer, sodium dithionite, and deionized water.

19 Claims, 2 Drawing Sheets

(56) References Cited

OTHER PUBLICATIONS

Mascal, Mark, "5-(Chloromethyl)furfural (CMF): A Platform for Transforming Cellulose into Commercial Products", ACS Sustainable Chemical Engineering, 2019, pp. 5588-5601, vol. 7, Issue 6.
Tan, Jingjing, "Complete Aqueous Hydrogenation of 5-Hydroxymethylfurfural at Room Temperature over Bimetallic RuPd/Graphene Catalyst", ACS Sustainable Chemical Engineering, 2019, pp. 10670-10678, vol. 7, Issue 12.
Mascal, Mark, et al., "Direct, High-Yield Conversion of Cellulose into Biofuel", Angew. Chem., 2008, vol. 120, pp. 8042-8044.
Kasanneni Tirumala Venkateswara Rao, et al., "Green synthesis of heterogeneous copper-alumina catalyst for selective hydrogenation of pure and biomass-derived 5-hydroxymethylfurfural to 2,5-bis(hydroxymethyl)furan", Applied Catalysis A, General, Oct. 19, 2021, pp. 1-12.
Fulignatia, Sara, et al, "Insight into the hydrogenation of pure and crude HMF to furan diols using Ru/C as catalyst", Applied Catalysis A, General 578, Apr. 8, 2019, pp. 122-133.
Chimentao, R.J., et al., "Selective hydrodeoxygenation of biomass derived 5-hydroxymethylfurfural over silica supported iridium catalysts", Applied Catalysis B: Environmental 241, 2019, pp. 270-283.
Yu, Jun, et al., "NiBi intermetallic compounds catalyst toward selective hydrogenation of unsaturated aldehydes", Applied Catalysis B: Environmental 277, 2020, 119273, pp. 1-9.
Li, Xing-Long, et al., "A cobalt catalyst for reductive etherification of 5-hydroxymethyl-furfural to 2,5-bis(methoxymethyl)furan under mild conditions", Green Chemistry, Jan. 26, 2018, vol. 20, Issue 5, pp. 1095-1105.
Feng, Yunchao, et al., "Cu1—Cu0 bicomponent CuNPs@ZIF-8 for highly selective hydrogenation of biomass derived 5-hydroxymethylfurfural", Green Chemistry, Jul. 11, 2019, vol. 21, Issue 6, pp. 4319-4323.
Corresponding Chinese Patent Application No. CN202111298723, First Office Action, dated Dec. 15, 2022.
Corresponding Chinese Patent Application No. CN202111298723, Second Office Action, dated Jan. 19, 2023.
Corresponding Chinese Patent Application No. CN202111298723, Notice of Grant, dated Feb. 21, 2023.
Vicente, Ana l., "Oxidation of 5-Chloromethylfurfural (CMF) to 2,5-Diformylfuran (DFF)", Molecules, Feb. 20, 2017, vol. 22, Issue 2, p. 329.
Hu, Lei, et al., "Recent advances in catalytic transformation of biomass-derived 5-hydroxymethylfurfural into the innovative fuels and chemicals", Renewable and Sustainable Energy Reviews, Jul. 2017, pp. 230-257.
Wang, Tao, et al., "Catalytic transfer hydrogenation of biomass-derived furfural to furfuryl alcohol with formic acid as hydrogen donor over CuCs—MCM catalyst", Chinese Chemical Letters, Mar. 2021, vol. 32, Issue 3, pp. 1186-1190.
Corresponding International Patent Application No. PCT/CN2022/099830, International Search Report, date mailed Sep. 20, 2022.
Corresponding International Patent Application No. PCT/CN2022/099830, Written Opinion, date mailed Sep. 20, 2022.

* cited by examiner

METHOD FOR PREPARING 2,5-BISHYDROXYMETHYLFURAN USING 5-CHLOROMETHYLFURFURAL

RELATED APPLICATIONS

This application is a continuation of International patent application PCT/CN2022/099830, filed on Jun. 20, 2022, which claims priority to Chinese patent application 202111298723.0, filed on Nov. 4, 2021. International patent application PCT/CN2022/099830 and Chinese patent application 202111298723.0 are incorporated herein by reference.

FIELD OF THE DISCLOSURE

The present disclosure relates to the field of organic synthesis, and specifically relates to a method for preparing 2,5-bishydroxymethylfuran using 5-chloromethylfurfural.

BACKGROUND OF THE DISCLOSURE 2,5-Bishydroxymethylfuran (BHMF), a high value-added diol, has important applications in preparation and research of polyheterocyclic compounds in synthesis of fine chemicals, novel functionalized polyethers, polyurethanes, and drugs. Presently, a main raw material for synthesis of the BHMF is a biomass-based platform molecule, 5-hydroxymethylfurfural (HMF) (ACS Sustainable Chemistry & Engineering, 2021, 9(3): 1161-71; Applied Catalysis A: General, 2021, 609: 117892; Applied Catalysis B: Environmental, 2020, 277, 119273; ACS Sustainable Chemistry & Engineering, 2019, 7(12), 10670-8; Applied Catalysis a-General, 2019, 578, 122-33; Green Chemistry, 2019, 21(16), 4319-23; Applied Catalysis B: Environmental, 2019, 241, 270-83; Green Chemistry, 2018, 20(5), 1095-105). However, the existing raw materials for preparing the HMF are mainly high-cost materials, such as fructose, and there are difficulties of low yield and poor selectivity caused by directly preparing the HMF using cheap materials, such as cellulose and biomass, as the raw materials. In addition, the HMF is difficult to separate and purify due to instability and hydrophilicity thereof, and a process for preparing the BHMF using the HMF on a large scale is further limited.

5-Chloromethylfurfural (CMF) can be directly prepared using raw materials, such as fibers and biomass, with high yields under mild conditions. The CMF is more convenient to be separated and purified due to stability and hydrophobicity thereof, so CMF is considered as a novel biomass-based platform molecule to replace the HMF (ACS Sustainable Chemistry & Engineering, 2019, 7(6), 5588-601; Angew Chem, Int Ed, 2008, 47(41), 7924-6). However, relevant reports for directly converting the CMF into the BHMF using one step with a high selectivity are rarely disclosed.

Therefore, directly preparing the BHMF from the novel biomass-based platform molecule CMF instead of the HMF with high selectivity can not only greatly reduce production costs, but also provide a better prospect for industrialization.

BRIEF SUMMARY OF THE DISCLOSURE

An objective of the present disclosure is to provide a method for directly preparing 2,5-bishydroxymethylfuran using 5-chloromethylfurfural derived from biomass to overcome the deficiencies of the existing techniques, achieve reaction conditions that are mild, and achieve a yield that is high.

The following technical solution is used to solve the technical problem of the present disclosure:

The present disclosure discloses a method for preparing 2,5-bishydroxymethylfuran using 5-chloromethylfurfural, the method comprises adding the 5-chloromethylfurfural, a catalyst, a base neutralizer, sodium dithionite, and deionized water to a closed reactor, filling $H_2$ into the closed reactor, and reacting by stirring at a speed of 400-800 revolutions per minute (rpm), a reaction formula is shown in FIG. 1; and the catalyst is prepared by the following method: dispersing metal oxide in $RuCl_3 \cdot 3H_2O$ solution while stirring, adding $NaBH_4$ solution dropwise while stirring, and obtaining the catalyst by centrifugation, washing with the deionized water, and freeze-drying.

In a specific embodiment, a ratio of the 5-chloromethylfurfural and the deionized water is 1:50-250 g/mL, preferably 1:50-100 g/mL; a weight ratio of the 5-chloromethylfurfural and the catalyst is 1:0.5-1.5, preferably 1:1; a weight ratio of the 5-chloromethylfurfural and the sodium dithionite is 1:0.05-0.2, preferably 1:0.1; a molar ratio of the 5-chloromethylfurfural and the base neutralizer is 1:0.5-0.9, preferably 1:0.7; the filling $H_2$ into the closed reactor comprises filling the $H_2$ into the closed reactor until an initial pressure of $H_2$ is 2-5 MPa, preferably 4 MPa; and the reacting by stirring at a speed of 400-800 rpm comprises reacting by stirring at the speed of 400-800 rpm at a temperature of 40-80° C. for 0.5-8 hours, preferably at the temperature of 60-70° C. for 2-5 hours.

In a specific embodiment, the base neutralizer is calcium carbonate, potassium bicarbonate, or sodium bicarbonate, preferably calcium carbonate.

In a specific embodiment, a weight ratio of the metal oxide, the $RuCl_3 \cdot 3H_2O$, and the $NaBH_4$ is 1:0.05-0.2:0.05-2.

The present disclosure has the following advantages.

1. A raw material 5-chloromethylfurfural used in the present disclosure, can be directly prepared using raw materials, such as cellulose or biomass, with a high yield, and 5-Chloromethylfurfural is easily separated and purified to greatly reduce production costs of the raw materials. Therefore, the present disclosure provides a sustainable path using renewable resources in a preparation of 2,5-bishydroxymethylfuran.

2. A catalytic reaction system used in the present disclosure can efficiently convert the raw material 5-chloromethylfurfural into 2,5-bishydroxymethylfuran under mild conditions. The used catalyst is easily prepared, and the base neutralizer and an additive sodium dithionite are cheap and easily obtained.

DETAILED DESCRIPTION OF THE EMBODIMENTS

Figure 1:
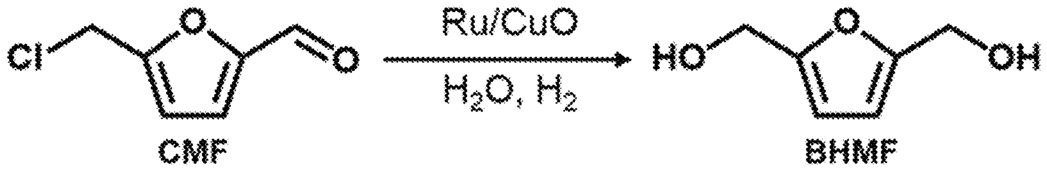
FIG. 1 illustrates a reaction pathway for preparing 2,5-bishydroxymethylfuran from 5-chloromethylfurfural.
Figure 3:
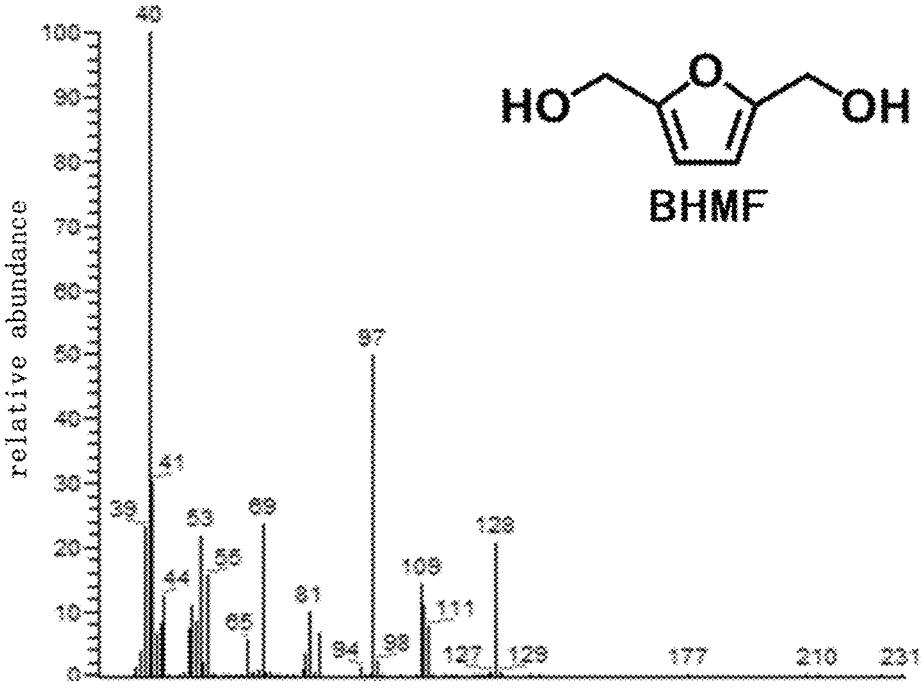
FIG. 3 illustrates a spectrum of 2,5-bishydroxymethylfuran prepared by Embodiment 16 of the present disclosure with gas chromatography-mass spectrometry (GC-MS).
Figure 2:
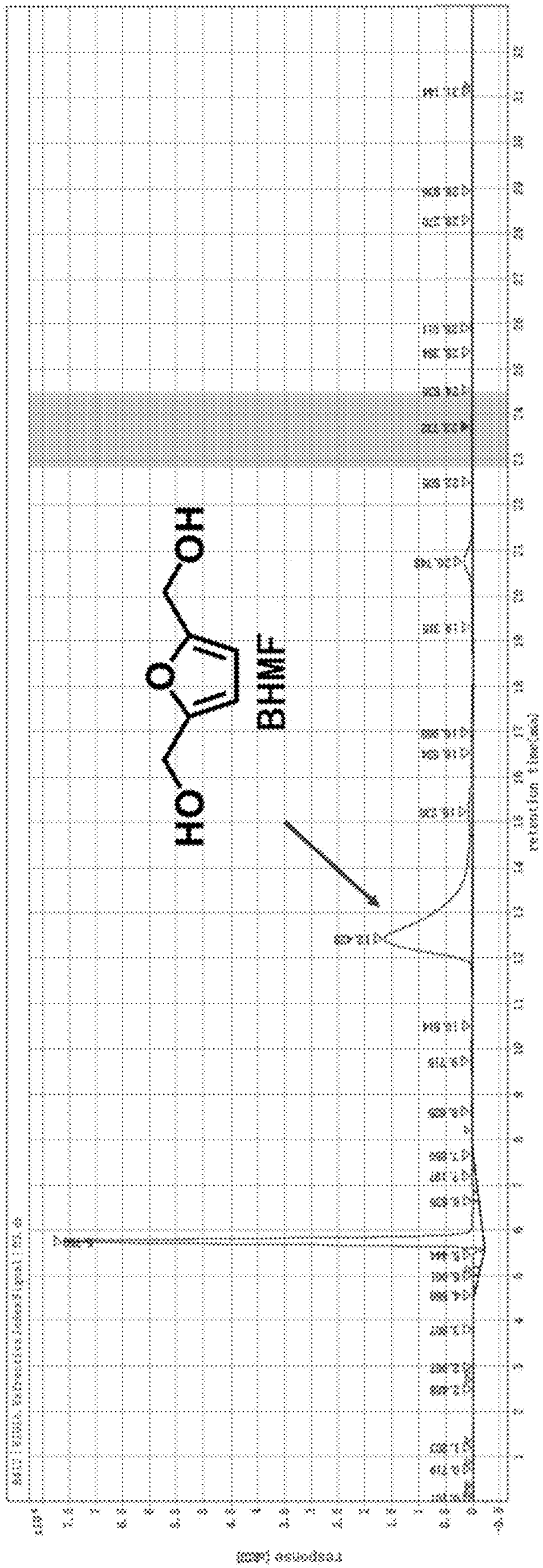
FIG. 2 illustrates a spectrum of 2,5-bishydroxymethylfuran prepared by Embodiment 16 of the present disclosure with high performance liquid chromatography (HPLC).

The present disclosure will be further described below in combination with the accompanying embodiment. Unless otherwise specified, the reagents and instruments used in the following embodiments are commercially available products. The specific embodiments are as follows:

Embodiment 1

Step 1) 0.103 g of $RuCl_3 \cdot 3H_2O$ is dissolved in 30 mL of deionized water to obtain a solution, and 1 g of CuO is then added to the aqueous solution and stirred for 2 hours. $NaBH_4$ solution (in which 0.3 g of $NaBH_4$ is dissolved in 20 mL of deionized water) is then added dropwise and stirred for 1 hour. A catalyst of Ru/CuO is obtained by centrifugation, washing using 30 mL of deionized water for 3 times, and freeze drying. A loading amount of Ru is 5 wt % Ru relative to a carrier of CuO.

Step 2) 0.1 g of 5-chloromethylfurfural, 0.1 g of the catalyst Ru/CuO, 0.05 g of calcium carbonate as a base neutralizer, 0.01 g of sodium dithionite, and 10 mL of deionized water are added to a stainless steel closed reactor, $H_2$ is filled into the stainless steel closed reactor until an initial $H_2$ pressure is 4 MPa, heated to 70° C. while stirring at a speed of 500 revolutions per minute (rpm), and reacted for 2 hours to obtain a reaction solution involving 2,5-bishydroxymethylfuran. After the reaction is complete, solid-liquid separation of the reaction solution involving 2,5-bishydroxymethylfuran is performed by a centrifuge machine at a speed of 8000 rpm for 5 minutes, and quantitative analysis is performed by high performance liquid chromatography (HPLC, Agilent 1260). Qualitative analysis is performed using gas chromatography-mass spectrometry (GC-MS, Thermo Scientific). The results are as follows: a molar yield of 2,5-bishydroxymethylfuran is 76%.

Embodiment 2

Step 1) The catalyst is prepared according to the method of Embodiment 1 for use. This embodiment differs from Embodiment 1 in that the carrier of the catalyst is $Co_3O_4$, so that a catalyst of Ru/$Co_3O_4$ is obtained. A loading amount of Ru is 5 wt % Ru relative to the carrier of $Co_3O_4$.

Step 2) The step 2 of Embodiment 2 is performed according to the step 2 of the method of Embodiment 1 using the catalyst of Ru/$Co_3O_4$. The results are as follows: a molar yield of 2,5-bishydroxymethylfuran is 34%.

Embodiments 3-6

Step 1) Four catalysts are prepared according to the method of Embodiment 1 for use. Embodiments 3-6 differ from Embodiment 1 in that 0.0205 g (1 wt %), 0.0616 g (3 wt %), 0.144 g (7 wt %), or 0.185 g (9 wt %) of $RuCl_3$-$3H_2O$ are added, respectively. The loading amount of Ru is 1 wt % Ru, 3 wt % Ru, 7 wt % Ru, or 9 wt % Ru relative to the carrier of CuO, respectively.

Step 2) The step 2 of each of Embodiments 3-6 is performed according to the step 2 of the method of Embodiment 1 using the four catalysts. The results are as follows: molar yields of 2,5-bishydroxymethylfuran are 13%, 39%, 74%, and 55%, respectively.

Embodiments 7-8

Embodiments 7-8 differ from Embodiment 1 in that the base neutralizer is $NaHCO_3$ and $KHCO_3$, respectively. The results are as follows: molar yields of 2,5-Bishydroxymethylfuran are 56% and 47%, respectively.

Embodiments 9-13

Embodiments 9-13 differ from Embodiment 1 in that the reaction for obtaining 2,5-bishydroxymethylfuran using 5-chloromethylfurfural is performed for 1 hour, 3 hours, 4 hours, 5 hours, and 6 hours, respectively. The results are as follows: molar yields of 2,5-Bishydroxymethylfuran are 51%, 78%, 81%, 76%, and 75%, respectively.

Embodiments 14-16

Embodiments 14-16 differ from Embodiment 1 in that the reaction for obtaining 2,5-bishydroxymethylfuran using 5-chloromethylfurfural is performed for 4 hours at 40° C., 50° C., and 60° C., respectively. The results are as follows: molar yields of 2,5-bishydroxymethylfuran are 28%, 73%, and 91%, respectively.

Embodiments 17-19

Embodiments 17-19 differ from Embodiment 1 in that the reaction for obtaining 2,5-bishydroxymethylfuran using 5-chloromethylfurfural is performed at 60° C. with the initial $H_2$ pressure of 2 MPa, 3 MPa, and 5 MPa for 4 hours. The results are as follows: molar yields of 2,5-bishydroxymethylfuran are 39%, 58%, and 84%, respectively.

The above-mentioned results are summarized in the following table:

TABLE 1

Effects of different types of catalysts and process variables on the hydrogenation yield of 5-chloromethylfurfural

| Embodiment | Catalyst | Loading amount of Ru (wt %) | Base neutralizer | Temperature (° C.) | Time (hour) | Pressure (MPa) | BHMF yield rate (%) |
|---|---|---|---|---|---|---|---|
| 1 | Ru/CuO | 5 | $CaCO_3$ | 70 | 2 | 4 | 76 |
| 2 | Ru/$Co_3O_4$ | 5 | $CaCO_3$ | 70 | 2 | 4 | 34 |
| 3 | Ru/CuO | 1 | $CaCO_3$ | 70 | 2 | 4 | 13 |
| 4 | Ru/CuO | 3 | $CaCO_3$ | 70 | 2 | 4 | 39 |
| 5 | Ru/CuO | 7 | $CaCO_3$ | 70 | 2 | 4 | 74 |
| 6 | Ru/CuO | 9 | $CaCO_3$ | 70 | 2 | 4 | 55 |
| 7 | Ru/CuO | 5 | $NaHCO_3$ | 70 | 2 | 4 | 56 |
| 8 | Ru/CuO | 5 | $KHCO_3$ | 70 | 2 | 4 | 47 |
| 9 | Ru/CuO | 5 | $CaCO_3$ | 70 | 1 | 4 | 51 |
| 10 | Ru/CuO | 5 | $CaCO_3$ | 70 | 3 | 4 | 78 |
| 11 | Ru/CuO | 5 | $CaCO_3$ | 70 | 4 | 4 | 81 |
| 12 | Ru/CuO | 5 | $CaCO_3$ | 70 | 5 | 4 | 76 |
| 13 | Ru/CuO | 5 | $CaCO_3$ | 70 | 6 | 4 | 75 |

TABLE 1-continued

Effects of different types of catalysts and process variables on the hydrogenation yield of 5-chloromethylfurfural

| Embodiment | Catalyst | Loading amount of Ru (wt %) | Base neutralizer | Temperature (° C.) | Time (hour) | Pressure (MPa) | BHMF yield rate (%) |
|---|---|---|---|---|---|---|---|
| 14 | Ru/CuO | 5 | $CaCO_3$ | 40 | 4 | 4 | 28 |
| 15 | Ru/CuO | 5 | $CaCO_3$ | 50 | 4 | 4 | 73 |
| 16 | Ru/CuO | 5 | $CaCO_3$ | 60 | 4 | 4 | 91 |
| 17 | Ru/CuO | 5 | $CaCO_3$ | 60 | 4 | 2 | 39 |
| 18 | Ru/CuO | 5 | $CaCO_3$ | 60 | 4 | 3 | 58 |
| 19 | Ru/CuO | 5 | $CaCO_3$ | 60 | 4 | 5 | 84 |

Based on the results of the above-mentioned embodiments, it is shown that the catalyst (Ru/CuO, especially when the loading amount of Ru is 5 wt % relative to carrier CuO) and the base neutralizer (especially $CaCO_3$) provided by the present disclosure can be effectively used in a preparation of 2,5-bishydroxymethylfuran (a high value-added fine chemical product) by hydrogenation of 5-chloromethylfurfural. The molar yield of 2,5-bishydroxymethylfuran is 91% under an optimal reaction condition, i.e., a temperature of the reaction is 60° C., a time of the reaction is 4 hours, and the initial pressure of $H_2$ is 4 MPa.

The embodiments are merely used for an objective of providing exemplary illustrations, and the protective scope of the present disclosure is not limited thereto in any way. Thus, it is intended that the protective scope of the present disclosure cover improvements and modifications provided they are improved or modified based on the aforementioned illustrations by person skilled in the art.

What is claimed is:

1. A method for preparing 2,5-bishydroxymethylfuran using 5-chloromethylfurfural, comprising:

adding the 5-chloromethylfurfural, a catalyst, a base neutralizer, sodium dithionite, and deionized water to a closed reactor, filling $H_2$ into the closed reactor, and reacting by stirring at a speed of 400-800 revolutions per minute (rpm), wherein the catalyst is a ruthenium-based metal oxide.

2. The method according to claim 1, wherein:

the catalyst is prepared by the following method:

dispersing metal oxide in $RuCl_3 \cdot 3H_2O$ solution while stirring, adding $NaBH_4$ solution dropwise while stirring, and obtaining the catalyst by centrifugation, washing with the deionized water, and freeze-drying, wherein the metal oxide is Cu oxide or Co oxide.

3. The method according to claim 2, wherein a weight ratio of the metal oxide, the $RuCl_3 \cdot 3H_2O$, and the $NaBH_4$ is 1:0.05-0.2:0.05-2.

4. The method according to claim 1, wherein a ratio of the 5-chloromethylfurfural and the deionized water is 1:50-250 g/mL.

5. The method according to claim 1, wherein a weight ratio of the 5-chloromethylfurfural and the catalyst is 1:0.5-1.5.

6. The method according to claim 1, wherein a weight ratio of the 5-chloromethylfurfural and the sodium dithionite is 1:0.05-0.2.

7. The method according to claim 1, wherein a molar ratio of the 5-chloromethylfurfural and the base neutralizer is 1:0.5-0.9.

8. The method according to claim 1, wherein:

the filling $H_2$ into the closed reactor comprises filling the $H_2$ into the closed reactor until an initial pressure of $H_2$ is 2-5 MPa, and the reacting by stirring at a speed of 400-800 rpm comprises reacting by stirring at the speed of 400-800 rpm at a temperature of 40-80° C. for 0.5-8 hours.

9. The method according to claim 1, wherein the base neutralizer is calcium carbonate, potassium bicarbonate, or sodium bicarbonate.

10. The method according to claim 1, wherein the closed reactor is a stainless steel closed reactor.

11. The method according to claim 1, wherein the catalyst is at least one of Ru/CuO or $Ru/Co_3O_4$.

12. The method according to claim 1, wherein the catalyst is Ru/CuO.

13. The method according to claim 2, wherein the metal oxide is CuO and $Co_3O_4$.

14. The method according to claim 1, wherein a ratio of the 5-chloromethylfurfural and the deionized water is 1:50-100 g/mL.

15. The method according to claim 1, wherein a weight ratio of the 5-chloromethylfurfural and the catalyst is 1:1.

16. The method according to claim 1, wherein a weight ratio of the 5-chloromethylfurfural and the sodium dithionite is 1:0.1.

17. The method according to claim 1, wherein a molar ratio of the 5-chloromethylfurfural and the base neutralizer is 1:0.7.

18. The method according to claim 1, wherein the reacting by stirring at a speed of 400-800 rpm comprises reacting by stirring at the speed of 400-800 rpm at a temperature of 60-70° C. for 2-5 hours.

19. The method according to claim 1, wherein the base neutralizer is calcium carbonate.

* * * * *